United States Patent [19]
Pazandak

[11] Patent Number: 4,708,138
[45] Date of Patent: Nov. 24, 1987

[54] ROTATING SURGICAL CUTTING KNIFE

[76] Inventor: Bradford B. Pazandak, 5421 La Sierra, Dallas, Tex. 75231

[21] Appl. No.: 545,967

[22] Filed: Oct. 27, 1983

[51] Int. Cl.[4] .................... A61B 17/32

[52] U.S. Cl. .................... 128/305; 604/22; 30/321

[58] Field of Search .................... 128/305, 304, 751–756; 30/321, 164.9, 123.3, 169, 164.95; 604/22

[56] References Cited

U.S. PATENT DOCUMENTS 3,787,972 1/1974 Carossino .................... 30/317
3,977,077 8/1976 Rebold .................... 30/321
4,180,075 12/1979 Marinoff .................... 128/305
4,368,734 1/1983 Banko .................... 128/305

*Primary Examiner*—Michael H. Thaler
*Attorney, Agent, or Firm*—George J. Brandt, Jr.

[57] ABSTRACT

A method is provided for performing an anterior capsulotomy as part of a cataract extraction. The instrument used comprises a cutting blade attached to a handle in such a way as to allow said blade to rotate 360 degrees. The shape and method of attachment of said cutting blade to said handle provides that the blade orients itself with the cutting edge forward in the direction of movement of the blade.

10 Claims, 6 Drawing Figures

26
25

ROTATING SURGICAL CUTTING KNIFE

BACKGROUND OF THE INVENTION

This invention relates to a method for performing an anterior capsulotomy during a cataract extraction and particularly to a method using an instrument designed to make the task simpler and more adequate.

In the past decade cataract extraction by the extracapsular technique has returned as a common method of cataract extraction, replacing in part intracapsular cataract extraction method. During extracapsular cataract extraction the anterior capsule of the lens is incised to allow its removal and to allow access to the underlying cortex and nucleus of the lens for their eventual removal. The most common method used today for an anterior capsulotomy is to use a small sharp hook called a cystotome. Through a small incision in the peripheral cornea, small connecting tears are made in the anterior lens capsule in a circular pattern around the periphery of the lens capsule. When a complete circle has been made by connecting the tears, the anterior capsule of the lens is free to be removed.

The cystotome method is combersome, time consuming and leaves tags of anterior capsule which often interfere with later removal of the cortex of the lens. In addition, traction on one of these tags can lead to a tear extending posteriorly into the posterior capsule of the lens; this is a significant complication. Furthermore, during the anterior capsulotomy by this method the cystotome often inadvertently and unknowingly slips below the level of the capsule. The operator is then given the false impression that he is cutting anterior capsule when in fact he is making an incision in the subjacent lens cortex. As a result, an inadequate opening is made in the anterior capsule. Finally, when the pupil is small, the procedure by the cystotome method becomes very difficult.

If the central cornea is removed as during a cornea transplant a very large opening is made into the eye. Through this large opening a scissors or conventional knife can be used to make a smooth circular incision into the anterior capsule. This could circumvent many of the above mentioned problems. Such a large incision, however, is impractical for routine cataract extractions.

The method and instrument herein described are designed for a simple anterior capsulotomy which is both performed through a small incision and leaves behind a smooth circular anterior capsule edge.

SUMMARY OF THE INVENTION

A method and instrument for performing a simple anterior capsulotomy as part of a cataract extraction operation is provided. The instrument comprises a cutting blade which is attached to a handle in such a way as to allow said cutting blade to rotate around said handle 360 degress. The shape and method of attachment of said cutting blade to said handle provides that the blade orients itself parallel to the vector of said blade's motion. The blade handle assembly may be equipped with irrigation for maintaining the anterior chamber during the procedure.

This method comprises the steps of placing the instrument in the eye through a small 2-3 mm incision at the corneo-scleral junction. The blade engages the anterior capsule near its periphery and with a circular motion the instrument with the knife trailing is moved around the edge of the anterior capsule incising the capsule as the blade is moved. The instrument may be moved beneath the iris to allow a large capsulotomy in an eye with a small pupil. When a complete circular incision has been made the instrument is removed.

DESCRIPTION OF THE DRAWINGS

This invention may better be understood when taken in conjunction with the following detailed description,-wherein.

DESCRIPTION

This anterior capsulotomy instrument has as its essential feature a cutting blade which rotates and thereby orients itself for most effective cutting of the anterior capsule of the lens. It allows for a simple method of performing an anterior capsulotomy even in an eye with a small pupil and leaves behind a smooth circular edge of lens capsule. In this embodiment, the instrument portion of this invention comprises a handle portion and a rotating portion.

Figure 1:
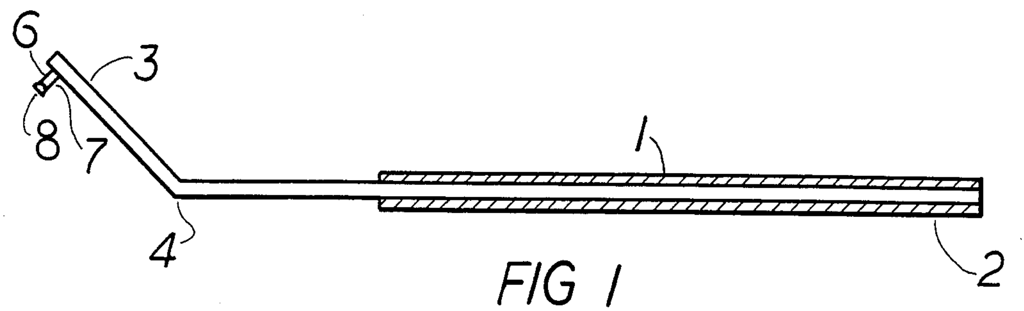
FIG. 1. is a cross-sectional view along the length of the pin-handle assembly of this invention.

The handle portion is a pin-handle assembly shown in FIG. 1. In this embodiment, it is a metal tube which tapers from the proximal hand held end (2) to the distal end (3). An optional bend (4) in the handle can be placed 5-15 mm from the distal end to aid its ease of use for some operators. From the inferior aspect of this tapered end extends a rigidly and perpendicularly attached pin (6) with shaft (7). At its unattached end the pin has a semi-circular enlargement (8) whose diameter is greater than the diameter of the shaft (7). In this embodiment the pin is metallic.

Because of the tubular construction of the handle and distal end, intervenous line tubing can be easily attached to the proximal end (2). Fluid can then flow through the handle and exit at the distal end outlet (5). This constant flow maintains the volume of the anterior chamber during the anterior capsulotomy.

Figure 2:
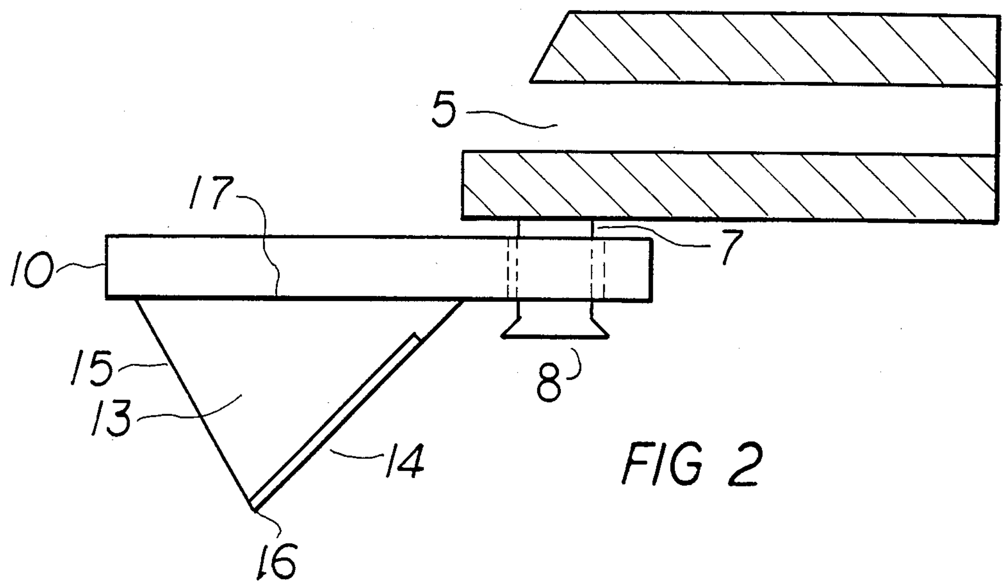
FIG. 2. is a cross-sectional view of the distal end of the assembled instrument.
Figure 6:
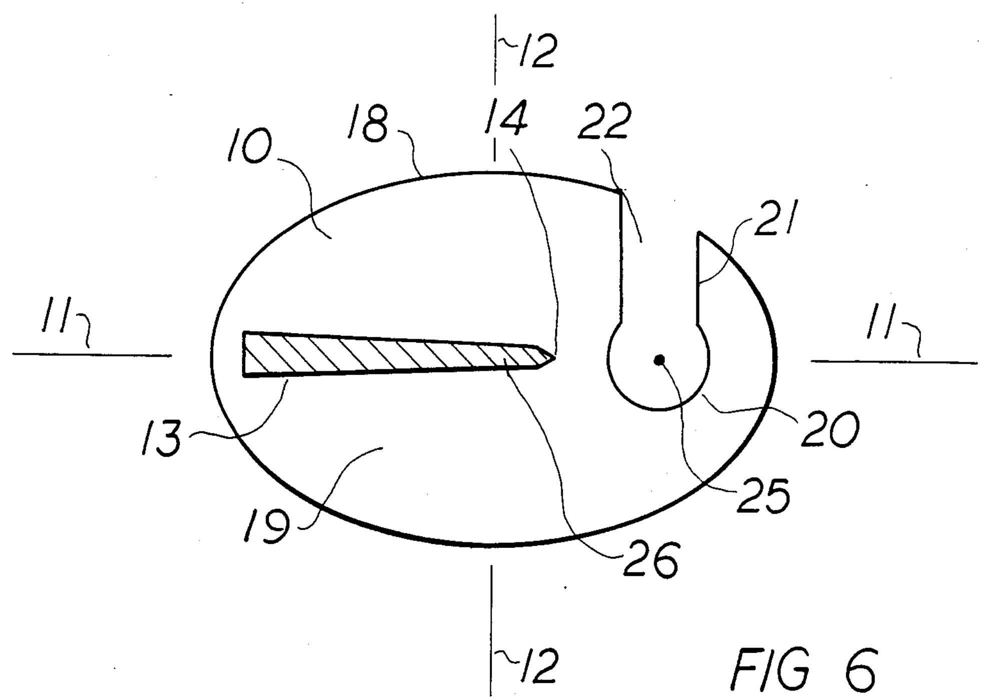
FIG. 6. is an elevational view of the rotating portion of this invention.

The rotating portion of this instrument is a plate-blade assembly as shown in FIGS. 2 and 6. In this embodiment both are metal. The plate (10) is ellipsoid in shape approximately 4-5 mm along its longer axis (11) and approximately 2 mm along the shorter axis (12). The cutting blade (13) is thin flat and triangular in shape with a cutting edge (14) and a non-cutting edge (15) converging to a point at a first blade end (16) and diverging to a flat second blade end (17). The cutting blade is attached to the plate along its second blade end (17). The attachment is perpendicular and rigid and is along a line through the long axis of the elliptical plate. The attachment is toward one end of the plate so that the non-cutting edge (15) is nearly adjacent to an edge of the plate. The areas of the plate between the blade and either of the longer sides (18) act like flanges and will be herein referred to as the flanges (19). There is a hole (20) through the plate through the line along the longer axis of the plate. This hole is positioned between the cutting edge of the blade and the edge of the plate. The hole is large enough to easily accomodate the shaft (7) of the pin (6) of the handle. A corridor (21) is cut from a side of the hole (2)which is smaller in width than the diameter of the hole. The corridor (21) connects a longer side of the plate (18) with the hole.

To assemble the instrument, the shaft (7) of the pin-handle assembly is placed over the external corridor area (22) of the blade-plate assembly. With forcefull pressure on the shaft, said shaft is snapped through the corridor into the hole. In the assembled position (FIG. 2.) the shaft is in the hole and yet free rotation of the blade-plate assembly around the pin is possible.

The method of this invention allows that the above assembled instrument be placed into the anterior chamber of the eye through a 3 mm incision at the corneoscleral junction (23). Once in the eye, downward pressure is exerted at the distal end of the handle which causes the blade to cut through the anterior capsule into the underlying cortex of the lens. The flanges on either side of the blade allow penetration into the cortex only as deep as the length of the blade. The flanges also prevent the blade from inadvertently falling below the level of the anterior capsule into the substance of the cortex when downward pressure is transferred to the blade-plate assembly from the handle.

Figure 4:
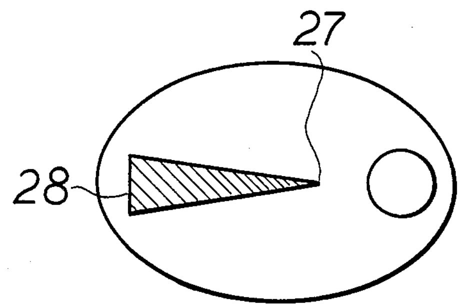
FIG. 4 is an elevational view of the rotating portion of a modification of this invention.
Figure 5:
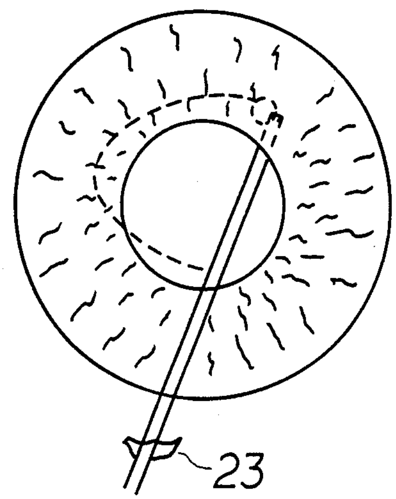
FIG. 5. is an elevational view illustrating the use of this instrument in the anterior chamber of an eye.

Linear movement of the distal end of the handle in the plane of and toward the periphery of the anterior capsule will cause rotation of the plate-blade assembly as shown in FIG. 5, so that the cutting edge is in the direction of movement. This forward orientation feature is an important part of this invention. This rotation is due to the displacement of the axis of rotation of the blade-plate assembly (25) away from the theoretical center of rotation of the blade-plate assembly (26). This displacement causes the assembly to rotate preferentially and align the blade-plate assembly with the cutting edge (14) forward in the direction of movement. This will insure a cutting action rather than a tearing action upon the anterior capsule. An obvious modification of this feature would be to construct the cutting edge (27) very thin and the non-cutting edge (28) substantially thicker as in FIG. 4. This construction would also orient the cutting edge properly.

When assembled the assembly is small enough that it can be inserted under the iris to accomplish an anterior capsulotomy in an eye with a small pupil.

Figure 3:
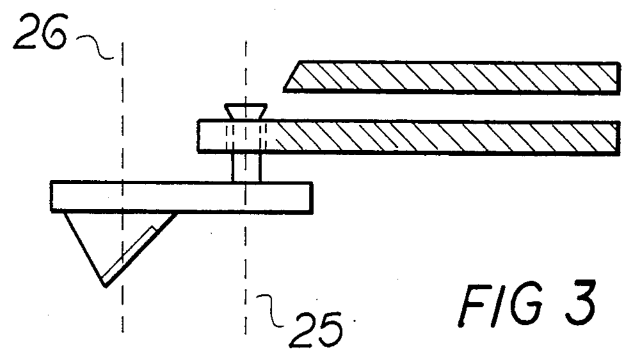
FIG. 3. is a cross sectional view of the distal end of a modification of this invention.

An obvious modification of this instrument is to rigidly attach the pin to the blade or the blade-plate assembly rather than the handle. This is shown in FIG. 3. Thus a hole could be fashioned in the distal end of the handle and allow for attachment, orientation and rotation of the blade.

What is claimed is:

1. A hand held surgical instrument for use in performing an anterior capsulotomy procedure incident a cataract extraction comprising an elongated handle having a proximal end to be grasped by the user during the procedure and a distal end, and a blade-plate assembly rotatably mounted to the handle distal end for rotation about an axis substantially perpendicular to said handle, said assembly including a blade having a cutting edge and a sharp point, the rotatable mounting location of said assembly being offset displaced from the geometric center of said assembly so that when the instrument distal end is inserted in the eye anterior chamber to engage the anterior capsule with the blade cutting edge and the handle manipulated linearly in the plane of the anterior capsule to move the said distal end thereof in a continuous circular course about the anterior capsule periphery, the blade cutting edge is caused to follow said distal end movement with preferential rotation of said assembly that aligns the cutting edge in the direction of handle distal end movement to correspondingly incise the anterior capsule in a circular cutting course.

2. The surgical instrument of claim 1 in which the handle is a tubular component whereby an eye irrigation fluid can be delivered through said handle to outlet at the distal end.

3. The surgical instrument of claim 1 comprising a shaft carried on the distal end of said handle extending substantially perpendicular thereto, the blade-plate assembly being received rotatably captured on said shaft.

4. The surgical instrument of claim 3 in which the shaft includes an enlarged tip end that captures the blade-plate assembly thereon.

5. The surgical instrument of claim 3 in which the blade-plate assembly includes a generally flat plate member, the plate being rotatable in a plane perpendicular to said shaft, the blade being fixed to said plate member such that its cutting edge is perpendicular to said plane.

6. The surgical instrument of claim 5 in which the plate member is oblong, there being a shaft receiving opening in said plate member adjacent one end thereof.

7. The surgical instrument of claim 5 in which said plate member opening communicates with a slotted corridor in said plate member extending to a margin thereof, the corridor having lesser dimension than the shaft size so that the blade-plate assembly can be removably snap fit to the shaft.

8. The surgical instrument of claim 7 in which the blade is a generally thin and of triangular profile in shape, the base of the triangle being connected to said plate member, one side of the triangle comprising the cutting edge and facing the said opening, the other side of said triangle being disposed adjacent the other end of said plate.

9. The surgical instrument of claim 5 in which the plate member is ellipsoid in shape and measures about 4 to about 5 mm. along to major axis and about 2 mm along its minor axis.

10. The surgical instrument of claim 5 in which the blade member is a relatively thin planar structure disposed along the long axis of the plate member, the plate member parts laterally of the blade member defining blade-plate assembly flanges which can engage the eye to limit the extent to which the blade can penetrate the cortex underlying the anterior capsule.

* * * * *